United States Patent
Joedicke et al.

(10) Patent No.: US 9,610,410 B2
(45) Date of Patent: Apr. 4, 2017

(54) DEVICE AND METHOD FOR ACTUATING A CARPULE

(75) Inventors: Thorsten Joedicke, Toennisvorst (DE); Berthold Lange, Werne (DE); Thomas Willms, Castrop-Rauxel (DE); Ying Yu, Dortmund (DE)

(73) Assignee: Boehringer Ingelheim MicroParts GmbH, Dortmund (DE)

( * ) Notice: Subject to any disclaimer, the term of this patent is extended or adjusted under 35 U.S.C. 154(b) by 749 days.

(21) Appl. No.: 14/002,024

(22) PCT Filed: Feb. 27, 2012

(86) PCT No.: PCT/EP2012/053249
§ 371 (c)(1),
(2), (4) Date: Oct. 24, 2013

(87) PCT Pub. No.: WO2012/116948
PCT Pub. Date: Sep. 7, 2012

(65) Prior Publication Data
US 2014/0114240 A1    Apr. 24, 2014

(30) Foreign Application Priority Data

Mar. 1, 2011  (EP) .................................... 11001664
May 12, 2011  (EP) .................................... 11003945

(51) Int. Cl.
*A61M 5/315*    (2006.01)
*A61M 5/24*    (2006.01)
(Continued)

(52) U.S. Cl.
CPC ...... *A61M 5/31596* (2013.01); *A61M 5/2448* (2013.01); *A61M 5/3146* (2013.01);
(Continued)

(58) Field of Classification Search
CPC ...... A61M 5/2448; A61M 2005/31598; A61M 5/2429; A61M 5/31528; A61M 3/005;
(Continued)

(56) References Cited

U.S. PATENT DOCUMENTS 4,874,381 A * 10/1989 Vetter ................... A61M 5/315
604/191
8,500,701 B2   8/2013 Kirchhofer
(Continued)

FOREIGN PATENT DOCUMENTS

DE         10340585 A1   4/2005
DE     102005063311 A1   8/2006
(Continued)

OTHER PUBLICATIONS

International Search Report for corresponding PCT Application PCT/EP2012/053249, dated Jun. 29, 2012.
(Continued)

*Primary Examiner* — Emily Schmidt
*Assistant Examiner* — William Frehe
(74) *Attorney, Agent, or Firm* — Michael P. Morris; Philip I. Datlow

(57) ABSTRACT

A device and a method are proposed for actuating a carpule, in which a piston is displaced in the carpule by means of a ram that is telescopically extensible by rotation, and in this way a liquid medicament formulation is expelled. For carrying out different processes, different operating movements are provided, particularly the operation of an operating element in different directions and/or the operation of different operating elements. This promotes simple, intuitive and safe operation.

9 Claims, 12 Drawing Sheets

(51) Int. Cl.
*A61M 5/31* (2006.01)
*A61M 35/00* (2006.01)

(52) U.S. Cl.
CPC ....... *A61M 5/31511* (2013.01); *A61M 35/003* (2013.01); *A61M 2005/2451* (2013.01); *A61M 2005/2474* (2013.01); *A61M 2005/31518* (2013.01); *A61M 2207/00* (2013.01)

(58) Field of Classification Search
CPC ................ A61M 5/2066; A61M 5/284; A61M 5/31596; A61M 5/3294; A61M 5/2422; A61M 5/281; A61M 5/283
See application file for complete search history.

(56) References Cited

U.S. PATENT DOCUMENTS

| | | | |
|---|---|---|---|
| 2005/0049951 A1 | 3/2005 | Kirchhofer | |
| 2006/0178638 A1 | 8/2006 | Reynolds | |
| 2007/0142789 A1 | 6/2007 | Fisher et al. | |
| 2008/0077095 A1* | 3/2008 | Kirchhofer | A61M 5/31551 604/246 |
| 2010/0087785 A1* | 4/2010 | Tschirren | A61M 5/2448 604/208 |
| 2011/0130723 A1* | 6/2011 | Hirschel | A61M 5/2033 604/187 |
| 2011/0152822 A1 | 6/2011 | Drunk et al. | |
| 2012/0209171 A1* | 8/2012 | Vedrine | A61M 5/284 604/87 |
| 2014/0114240 A1 | 4/2014 | Joedicke | |

FOREIGN PATENT DOCUMENTS

| | | |
|---|---|---|
| EP | 0328699 A1 | 8/1989 |
| JP | 2004535255 A | 11/2004 |
| WO | 2004078226 A2 | 9/2004 |
| WO | 2006058435 A2 | 6/2006 |
| WO | 2009153132 A1 | 12/2009 |
| WO | 2012116948 A1 | 9/2012 |

OTHER PUBLICATIONS

International Preliminary Report on Patentability for corresponding PCT Application PCT/EP2012/053249, dated Sep. 3, 2013.

* cited by examiner

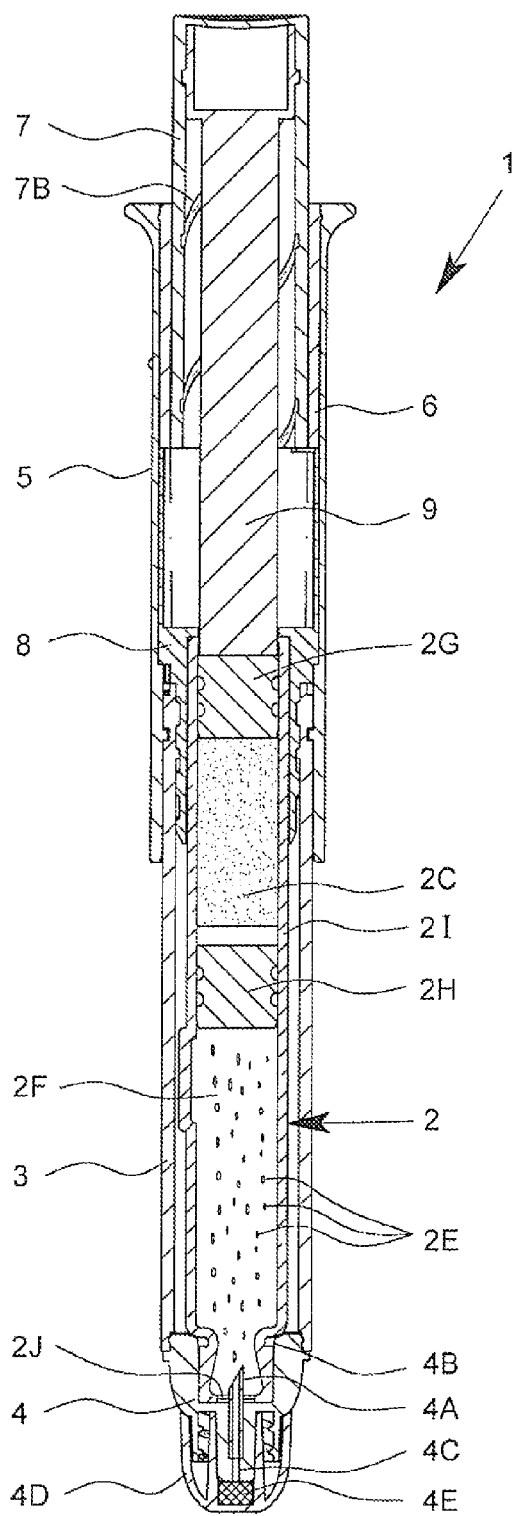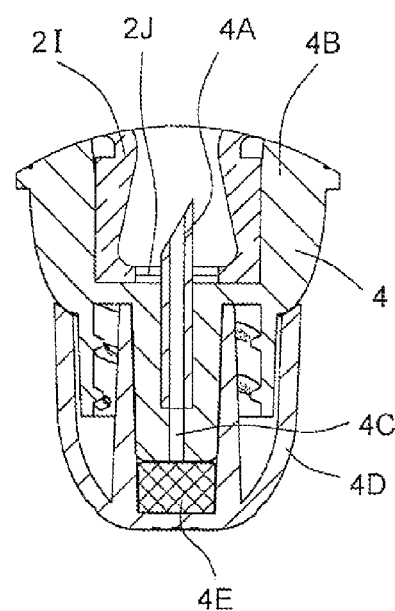
Fig. 12
Fig. 11

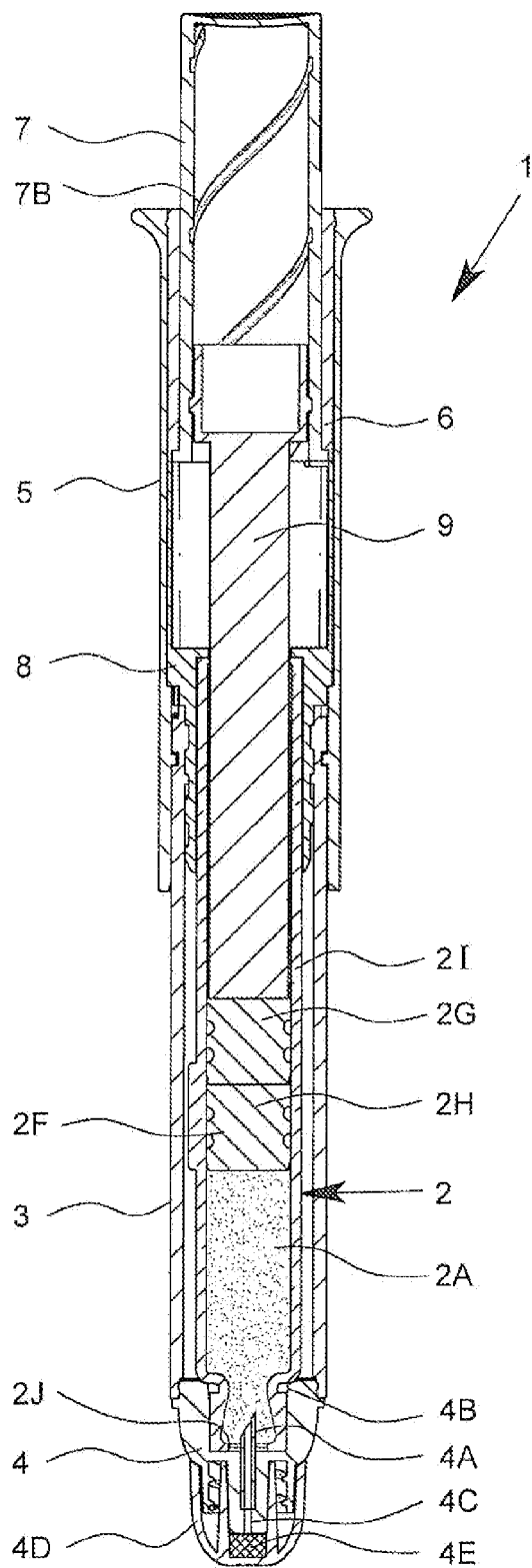
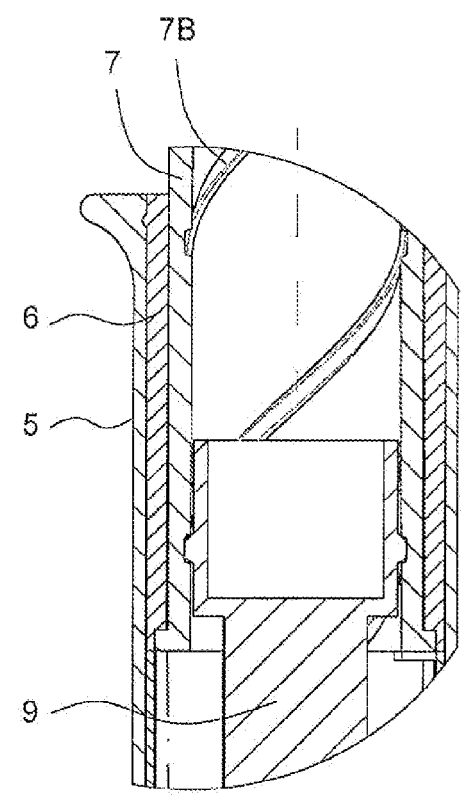
Fig. 16
Fig. 15

DEVICE AND METHOD FOR ACTUATING A CARPULE

The present invention relates to a device for receiving and actuating a carpule, and a method for actuating a carpule.

A carpule in the sense of the present invention is, more particularly, an ampoule containing a medicament formulation and having a piston that is movable therein. In a broader sense the carpule may also be, for example, a syringe or other medicament container.

By the term "medicament formulation" and "medicament" are meant, besides medication, in the present invention, therapeutic agents, diagnostic agents or the like, thus in particular any type of agent for injection.

The medicament or medicament formulation may already be present in the carpule in liquid form. In this case the liquid medicament formulation will be expelled through an outlet by means of the piston when the carpule is actuated, in particular by pushing the piston.

The medicament formulation or a medicament or active substance may however also be present in the carpule in dry form and be mixed first of all with a solvent or liquid before it is administered or expelled. In this case it is, in particular, a multi-chamber carpule as known, for example, from DE 103 40 585 A1 or WO 2008/148518 A1. The liquid or the solvent is held in a chamber in the carpule and, when the piston is pushed, it is transferred into another chamber containing the medicament or active substance and mixed therewith. In this way the liquid medicament formulation is formed in the carpule in a mixing process or mixing step—referred to here as "mixing" for short—and then expelled or administered as the piston is pushed further.

Known devices for receiving and actuating a carpule comprise a ram for actuating or moving the piston of the carpule. However, the known devices are not ideal in their structure and operation.

The present invention is based on the problem of providing a device and a method for actuating a carpule, by which a simple, robust and/or compact construction for holding the carpule preferably in its entirety is obtained and/or a very simple and/or reliable operation is assisted or made possible.

According to one aspect of the present invention a ram that actuates the carpule or moves a piston of the carpule is telescopically extended by rotation. In particular, the ram is of multi-part configuration for this purpose. This contributes to ease of handling as the axial stroke of an operating element that normally accompanies the axial displacement of the piston can be minimised or reduced in accordance with the telescopic extension. Moreover, a simple, robust and/or compact construction is made possible.

In another aspect of the present invention, a plurality of different operating movements, preferably taking place in different directions, in particular at least one rotary movement and one axial movement, are combined or are necessary in order to operate the device or actuate the carpule or move the piston. This allows simple, intuitive and/or reliable operation, particularly in multi-stage procedures, particularly preferably comprising a mixing operation in the carpule. In particular, different processes such as the opening or piercing of the carpule, mixing, priming (expulsion of air) and expulsion of the liquid medicament formulation are carried out or effected by different operating movements.

According to another aspect of the present invention an operating element of the device can be rotated in opposite directions one after the other, in order to actuate the carpule and/or effect different actuations or processes in the carpule.

Preferably, a dry medicament formulation is first dissolved by or in a liquid solvent in the carpule and then the solvent is delivered or expelled with the dissolved medicament formulation. Thus on the one hand the advantages of a dry medicament formulation, for example its good storage stability, and on the other hand the advantages of a liquid medicament formulation or liquid medicament supply can be achieved. For example, it is also possible to mix two liquids and/or liquid medicament formulations in the carpule before expulsion.

The aspects and features of the present invention mentioned above and the aspects and features of the present invention that are apparent from the following description and the claims may be combined with one another as desired but may also be realised independently of one another.

Further aspects, features, properties and advantages of the present invention will become apparent from the claims and the following description of a preferred embodiment by reference to the drawings, wherein:

FIG. 4 is a perspective view of a top part of the device with the cover put on;

FIG. 11 is a schematic section through the device after the carpule has been opened;

FIG. 12 is a detailed enlargement of FIG. 11 in the region of the top part or front end;

FIG. 15 is a schematic section through the device after the mixing of liquid and medicament in the carpule;

FIG. 16 is an enlarged detail of FIG. 15 in the region of the transition from the rear part to the actuating part;

Figure 1:
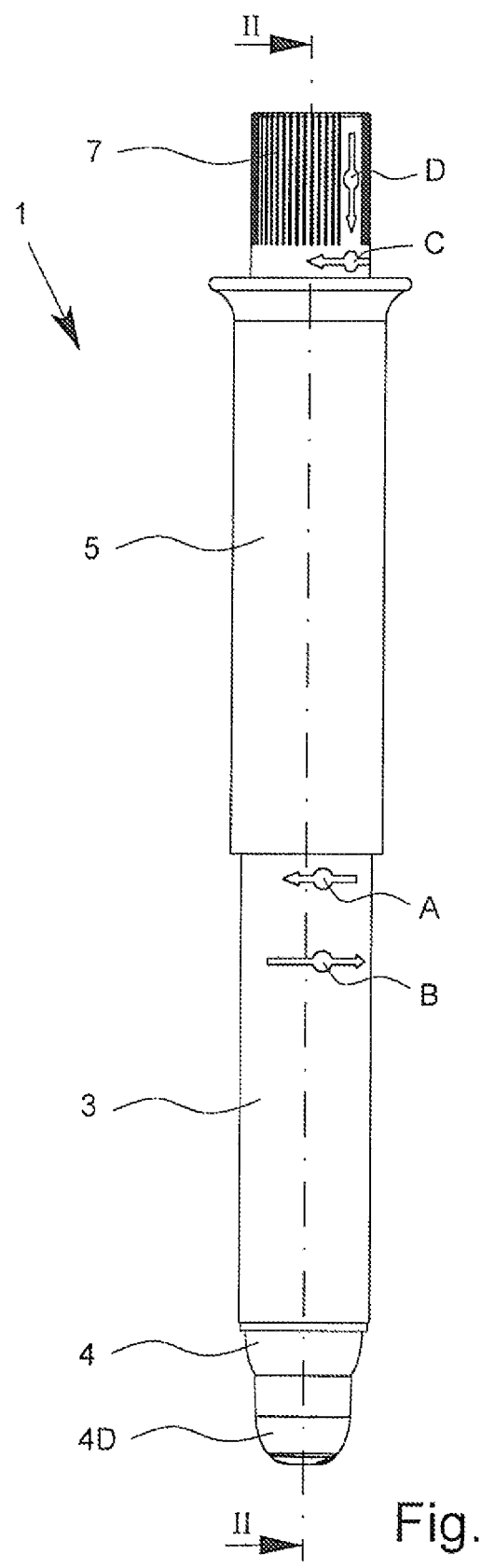
FIG. 1 is a schematic representation of a proposed apparatus in the preassembled state with the carpule inserted.
Figure 2:
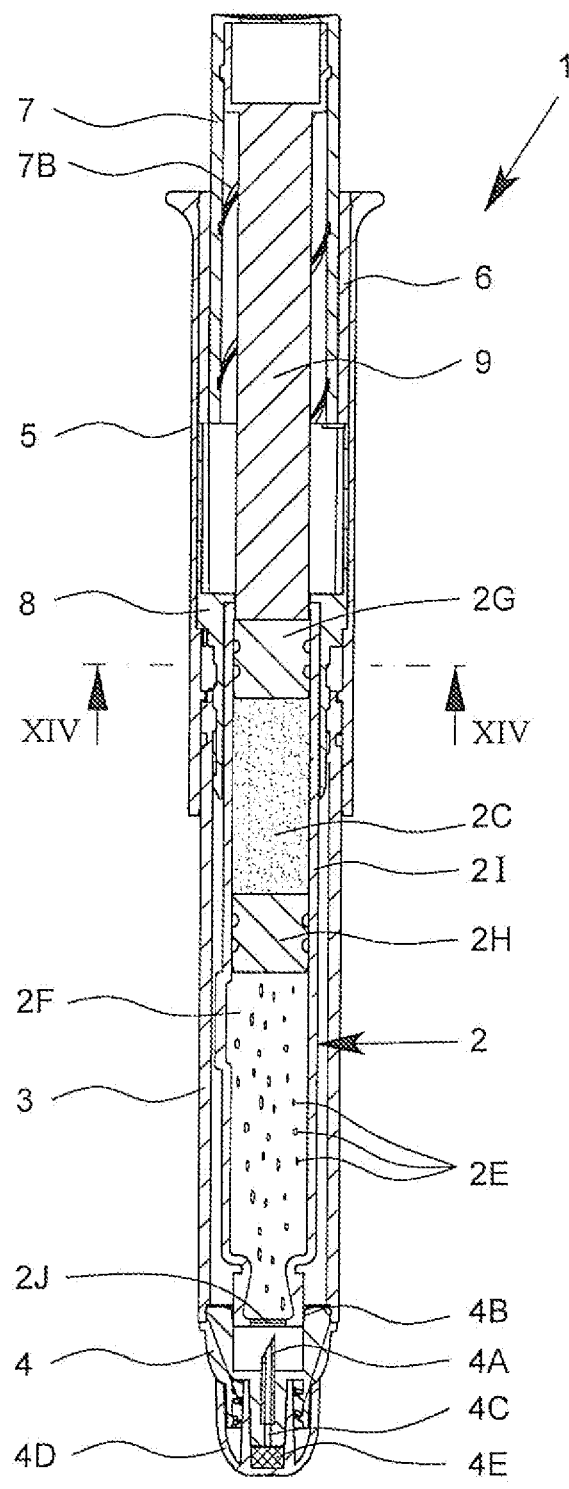
FIG. 2 is a schematic section through the apparatus according to FIG. 1.
Figure 3:
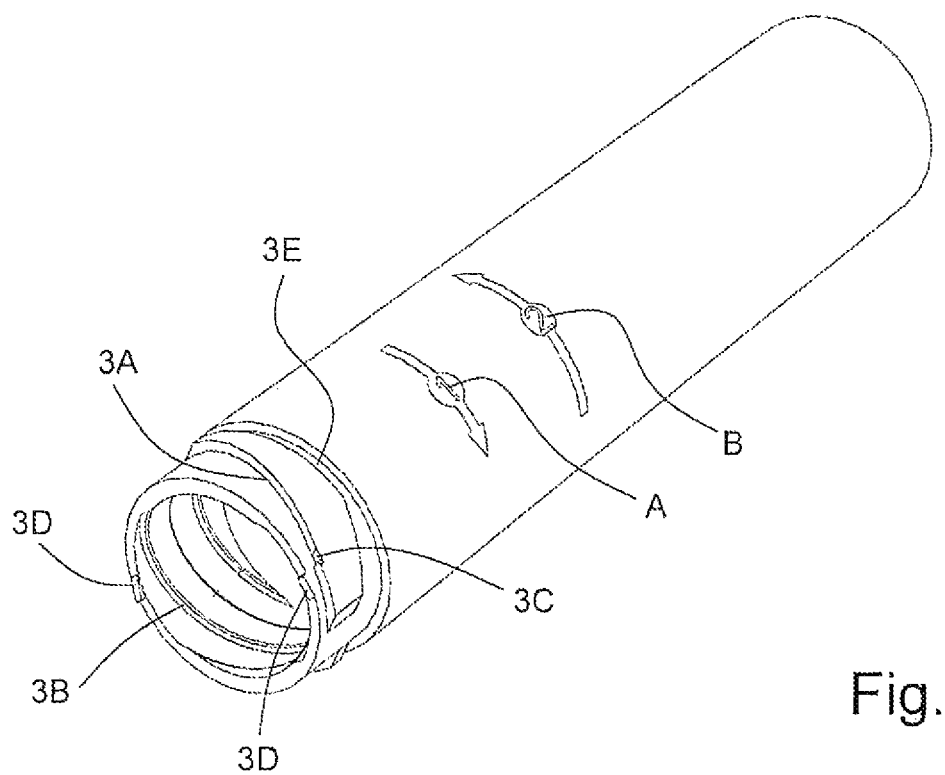
FIG. 3 is a perspective view of a front part of the device.
Figure 4:
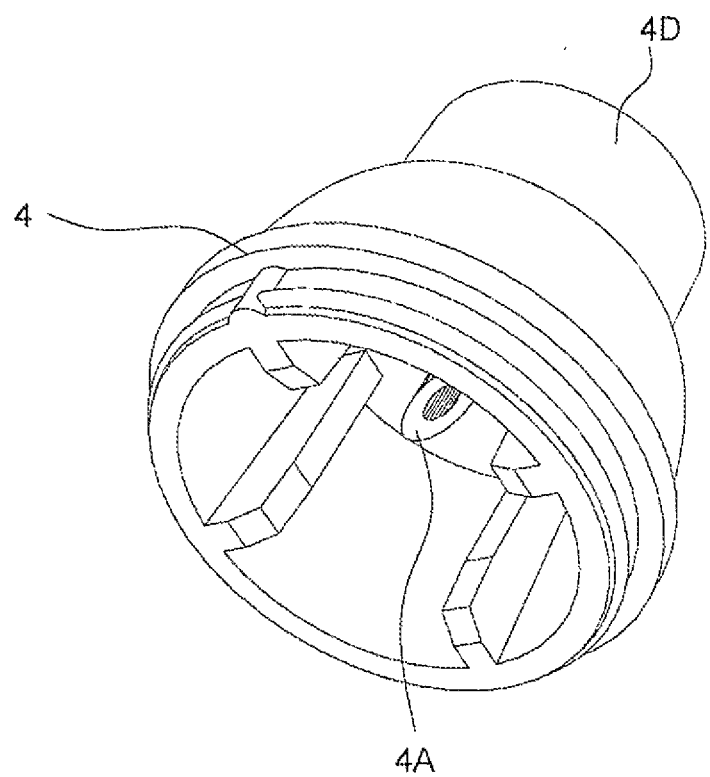
Figure 5:
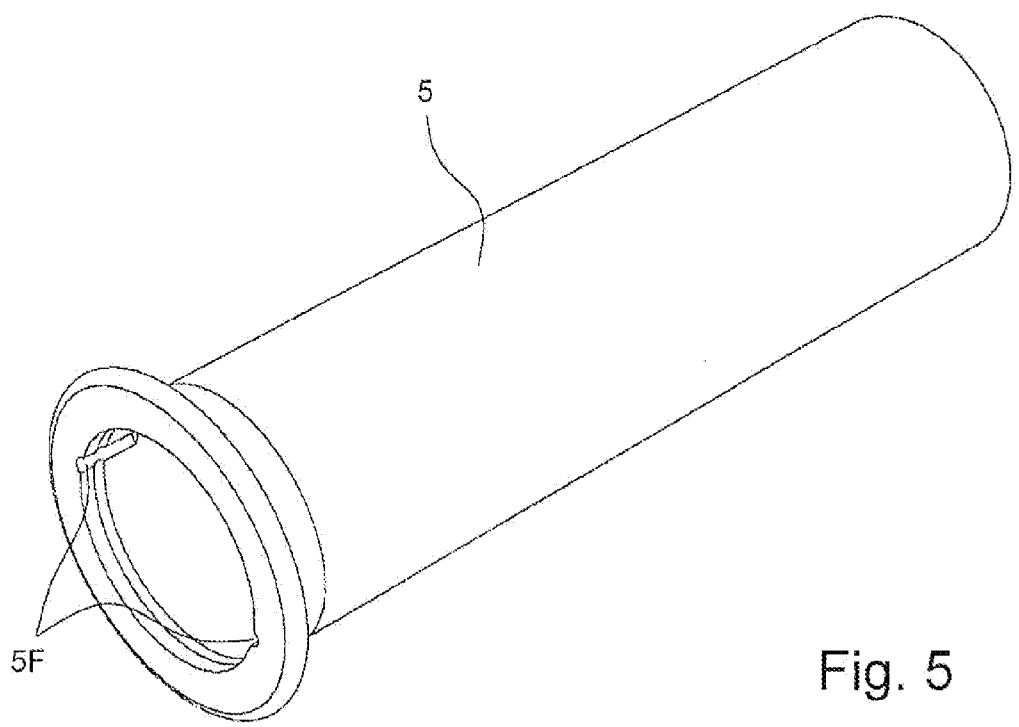
FIG. 5 is a perspective view of a central part of the device.
Figure 6:
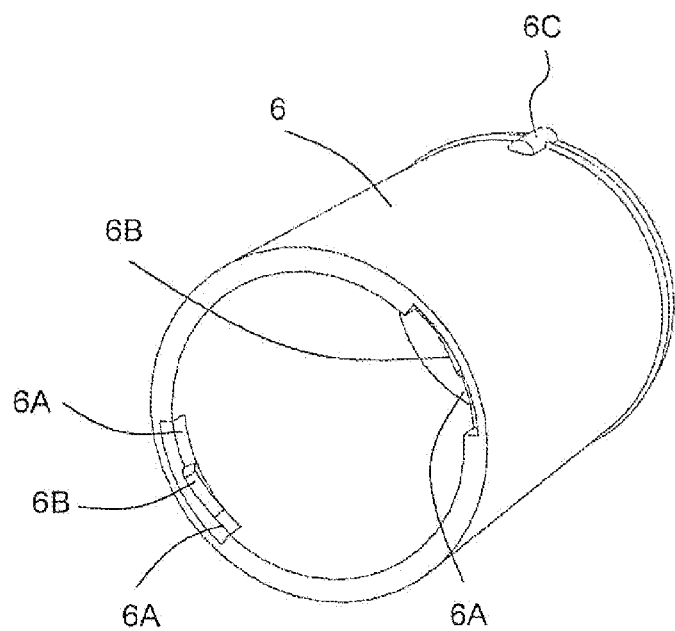
FIG. 6 is a perspective view of an insert of the device.
Figure 7:
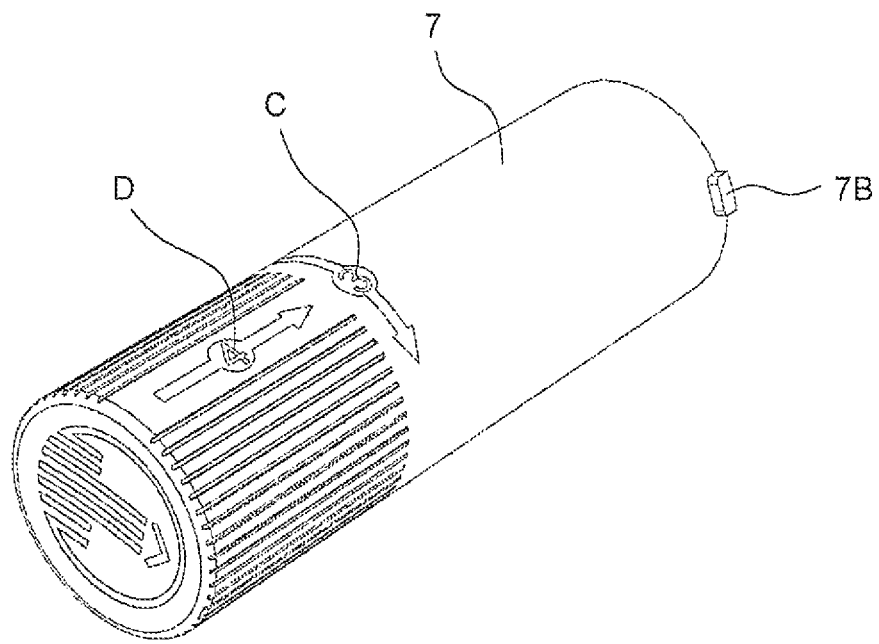
FIG. 7 is a perspective view of a rear part of the device.
Figure 8:
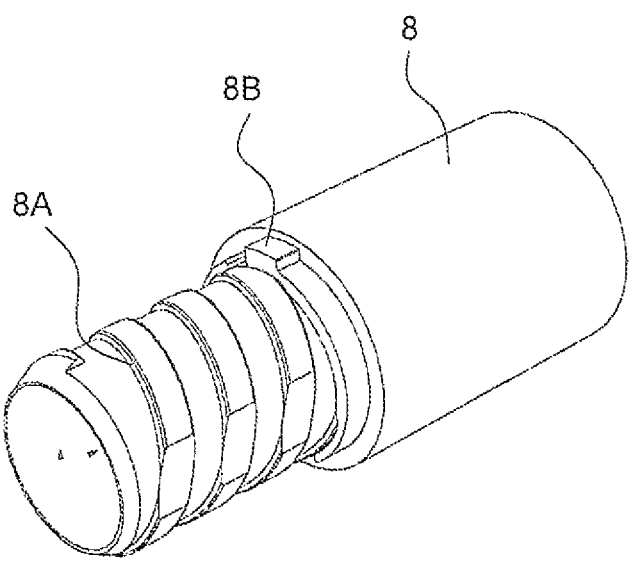
FIG. 8 is a perspective view of an inner part of the device.
Figure 9:
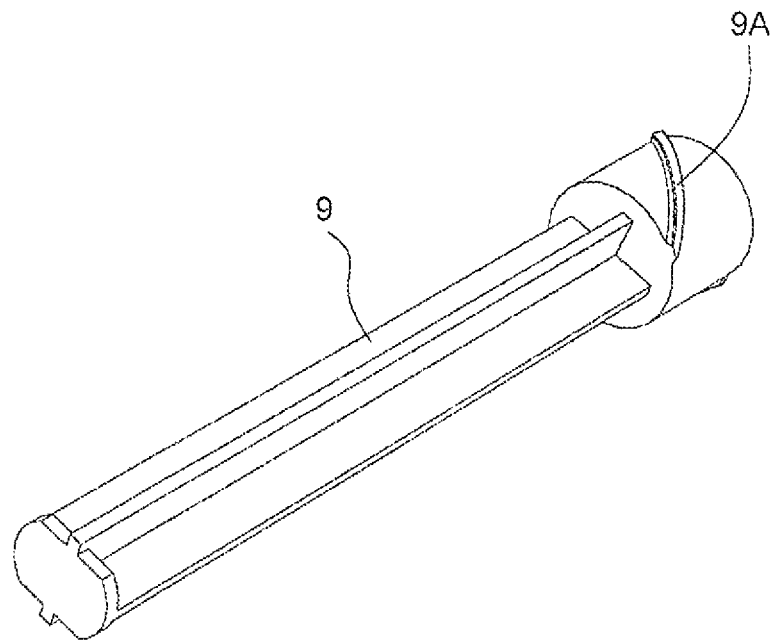
FIG. 9 is a perspective view of an actuating part of the device.

A device 1 as proposed is shown in schematic side view in FIG. 1 and in schematic section in FIG. 2. The device 1 is shown in the preassembled or already mounted state, in which a carpule 2, particularly in the sense referred to hereinbefore or some other medicament container, is already held or inserted in the device 1, as is apparent from the section in FIG. 2.

Figure 18:
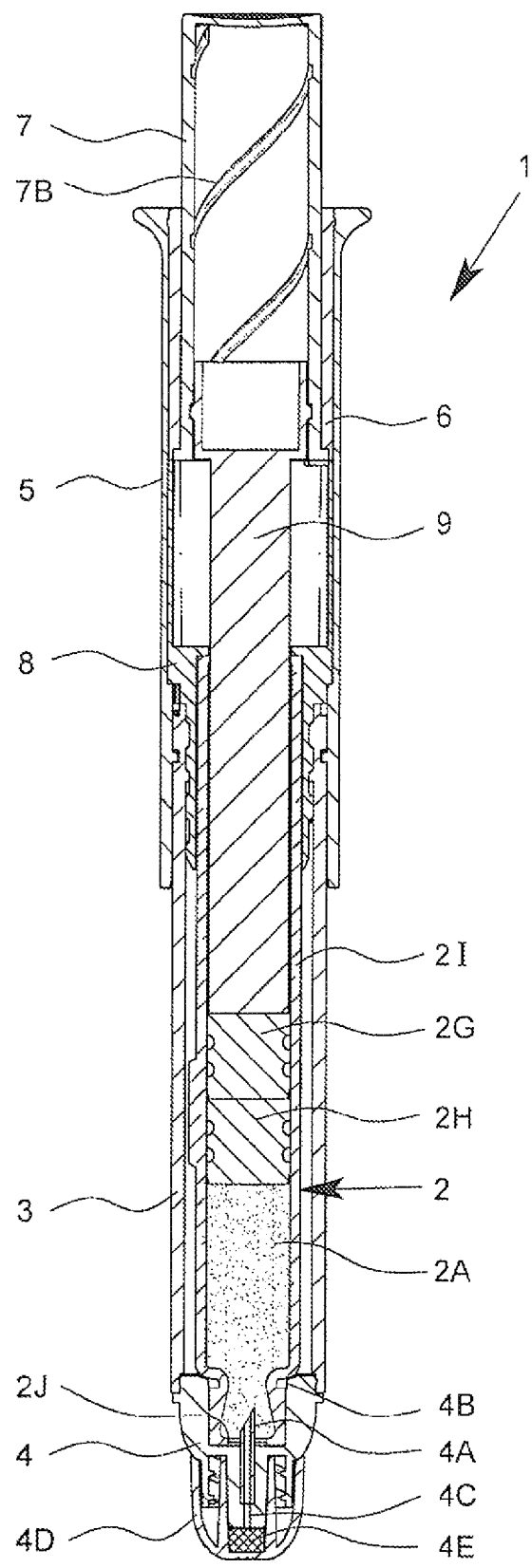
FIG. 18 is a schematic section through the device after priming.

The carpule 2 serves to provide a liquid medicament formulation 2A as indicated in FIGS. 15 and 18, which can be delivered or expelled by means of the device 1, in particular by corresponding operation of the device 1 and resulting (preferably manual) actuation of the carpule 2.

In the embodiment shown the carpule 2 is preferably embodied as a multi-chamber carpule. It comprises a first chamber containing a solvent or a liquid 2C and a second chamber containing a liquid active substance or medicament 2E that is separate from the liquid 2C, particularly dry or optionally also liquid, as shown in FIG. 2. In a mixing operation or transfer step (referred to as "mixing" for short) the liquid 2C may flow preferably by means of an overflow channel 2F from the first chamber into the second chamber 2D and dissolve the medicament 2E in order to form the liquid medicament formulation 2A initially in the carpule 2. Then this medicament formulation 2A can be delivered or expelled.

The carpule 2 preferably comprises a first piston 2G and particularly preferably a second piston 2H. In the delivered state or in the unused state the liquid 2C is held in the first chamber, particularly between the two pistons 2G and 2H. However, other embodiments are also possible, for example instead of the overflow channel 2F and/or second piston 2H for example a membrane or valve arrangement or the like may be provided.

The preferably dry or dried medicament 2E may be for example a lyophilisate with a corresponding active substance or the like. The dry medicament 2E is preferably present in dried form and/or in powder form, pellet form or the like.

In the embodiment shown, the liquid medicament formulation 2A is not mixed or prepared until the carpule 2 is used or actuated. However, the carpule 2 may theoretically contain the liquid medicament formulation 2A already premixed or already in liquid form. For example, the carpule 2 may also be embodied as a single-chamber carpule. The proposed device 1 can preferably be used for this as well, with the result that the explanations that follow then apply accordingly, in particular.

The carpule 2 comprises a housing 2I that is preferably substantially hollow-cylindrical and/or elongate.

The pistons 2G, 2H are preferably movably guided within the carpule 2 or its housing 2I. In particular, the carpule 2 is embodied to be open or openable on an actuating side, at the upper end in the representation shown in FIG. 2, so that it is possible to actuate the carpule 2 by acting upon the first piston 2G, particularly preferably by pressing or displacing the piston 2G.

The carpule 2 is (initially) closed off at the outlet end, particularly at an end opposite the actuating end, in this case the front or lower end, by an openable closure 2J such as a septum, a membrane or the like, in the delivered state and in the installed state shown in FIGS. 1 and 2.

In the embodiment shown the device 1 preferably comprises a front part 3, a top part 4, a central part 5, an insert part 6, a rear part 7, an inner part 8 and/or an actuating part 9, as shown particularly in the perspective views in FIGS. 3 to 9.

The device 1 is preferably embodied to open or pierce the carpule 2 or the closure 2J. For this purpose the device 1 or its top part 4 preferably comprises an opening or piercing element 4A, in the form, for example, of an inwardly facing cannula 4A or the like, as shown in FIG. 2. The piercing element 4A is preferably held by the top part 4 in the embodiment shown or is cast into the latter.

To prevent unintentional opening or piercing of the carpule 2 in the preassembled or installed state, the device is preferably embodied such that the carpule 2 is held by interlocking and/or frictional engagement with the closure 2J at a spacing from the piercing element 4A. In the embodiment shown, the device 1 or its top part 4 has an optionally somewhat conically shaped ring section 4D which frictionally holds the carpule 2 particularly on the outside or at the bottom end or outlet end at a spacing from the piercing element 4A such that the closure 2J is not accidentally or prematurely opened or pierced.

In the embodiment shown the device 1 or its top part 4 has an outlet 4C which is preferably fluidically adjacent to the cannula and/or serves to deliver the liquid medicament formulation 2A. The outlet 4C is preferably embodied as a standard connection, for example for attachment to a catheter or the like (not shown).

The device 1 or its top part 4 or the outlet 4C is preferably initially covered by a removable cover 4D and/or an intake member 4E. The intake member 4E is preferably of sponge-like configuration and/or is held or received by the cover 4D. The cover 4D is in turn preferably fitted in latching or clamping manner on the top part 4 or on the device 1. However, it may also be screwed on or attached in some other way.

The top part 4 is preferably in the form of a lid or cap.

The front part 3 of the device 1 is preferably at least substantially sleeve-shaped and/or hollow-cylindrical in form.

The front part 3 preferably forms a first operating element of the device 1. This will be described in more detail hereinafter.

The front part 3 is connectable to the central part 5 and together with the latter preferably forms an at least substantially elongate or cylindrical housing of the device 1.

The housing part 5 is in particular at least substantially sleeve-shaped and/or hollow-cylindrical in form.

In the preassembled state the housing part 3 is already attached to the central part 5, particularly by a corresponding screw fixing. In the embodiment shown the front part 3 preferably comprises at its end facing the central part 5 an external thread 3A for direct connection or screwing to the central part 5. In particular, the central part 5 can engage with or be connected to the external thread 3A by means of corresponding internal projections or an internal thread 5A, as shown purely schematically in FIG. 2.

Figure 14:
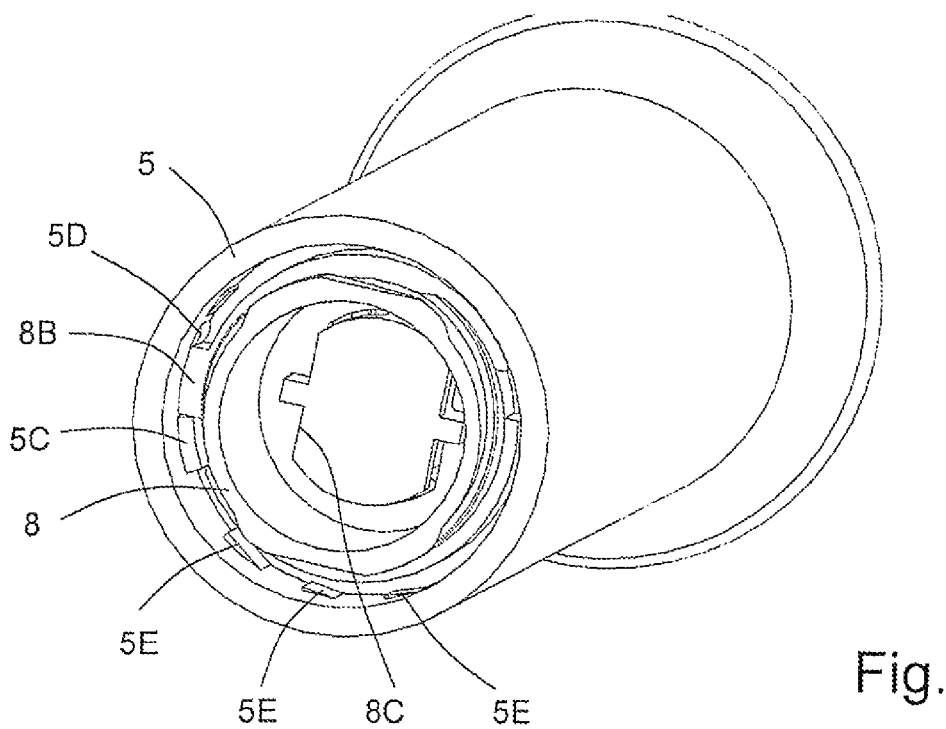
FIG. 14 is a schematic section through the device according to FIG. 2 along the line XIV-XIV.

Alternatively or additionally, the front part 3 may be, or may already have been, connected, particularly screwed, to the inner part 8 particularly by means of the internal thread 3B, the inner part 8 in turn preferably having been (axially) supported or (rotatably) mounted in and/or on the central part 5, particularly preferably so as to be rotatable in only one direction, as shown in FIG. 14, which will be described in more detail hereinafter. The inner part 8 therefore preferably has a corresponding external thread (8A as indicated particularly in FIG. 8, for connecting to the internal thread 3B of the front part 3.

For assembling the device 1, two assemblies or units are preferably formed to begin with, namely a first unit consisting of the front part 3 and top part 4 and a second unit consisting of the other parts 5 to 9.

The insert 6 is preferably embodied to be at least substantially sleeve-shaped or hollow-cylindrical in form.

The insert 6 preferably comprises at least one radial projection 6C, in the embodiment shown two radial projections 6C, for connection to the housing part 5 for rotation therewith. In particular, the projections 6C engage in corresponding axially open recesses 5F in the central part 5 when the insert 6 is axially inserted or engaged in the central part 5.

Before the insert 6 is inserted in the central part 5, the rear part 7 is preferably inserted in the insert 6 from below, so that the projections 7B come to rest in the recess 6A. Moreover, the inner part 8 is inserted in the central part 5 beforehand from the rearward end, or the end nearest the rear part, of the central part 5. Then the insert 6 can be installed or inserted in the central part 5 together with the actuating part 9 that is screwed into the rear part 7. Thus a simple assembly is obtained.

After the preassembly of the two units mentioned above, the carpule 2 is inserted, in particular into the central part 5 or inner part 8 initially. Then the two units are joined together, particularly screwed together. Particularly preferably, the front part 3 is pushed onto the carpule and screwed to the central part 5 and/or inner part 8 until the preassembled state is achieved.

Figure 10:
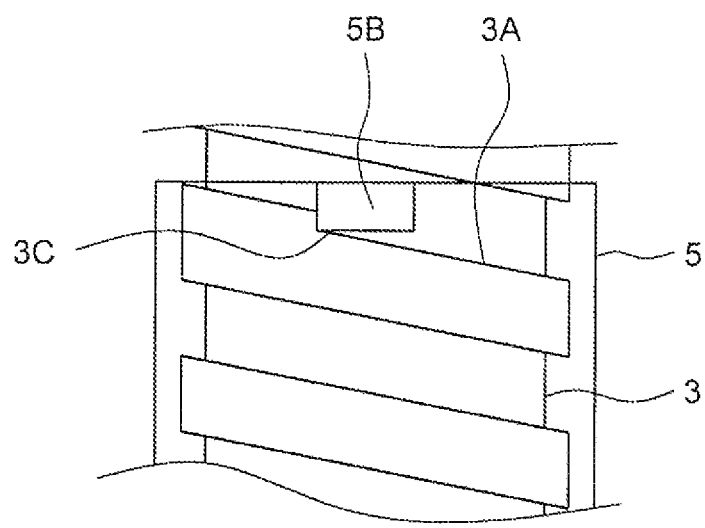
FIG. 10 is a schematic detailed view of the latching of the front part to the central part in the preassembled state.

For screwing together, the housing part 3 is preferably rotated in the direction of the arrow A, as shown in FIG. 1, relative to the central part 5. However, the threaded part 3 is preferably not screwed tight or screwed in fully, but rather only tightened until the preassembled position is reached (an intermediate position). This preassembled position is indicated particularly by a (first) detent, as shown by way of example in FIG. 10. An internal projection 5B on the central part 5 engages here on or in a latching recess 3C on the front part 3, particularly on a thread turn of the external thread 3A. The latching recess 3C or the latching means is preferably embodied such that the achievement of this latching position or the preassembled position is indicated by a "click" or other noise, and/or that reverse rotation is no longer possible, but it is only possible to rotate in direction A, after overcoming a corresponding force, for example with corresponding deformation, i.e. it is only possible to continue screwing the front part 3 to the central part 5 and/or inner part 8.

Starting from the preassembled or installed state, the actuation or use of the carpule 2 and in particular the operation of the device 1 is preferably subdivided into four sections, steps or operations, namely: first, opening (piercing of the carpule 2 or closure 2J); secondly, mixing (transferring the liquid 2C from the first chamber into the second chamber 2D or into the medicament 2E); thirdly, priming (expelling air from the carpule 2, the top part 4, the cannula 4A and/or the outlet 4C); and fourthly, expelling (delivering the liquid medicament formulation 2A through the outlet 4C or via the top part 4 out of the device 1).

For the opening, a first operation of the device 1 or an operating movement is carried out in direction A, i.e. as indicated by arrow A in FIG. 1. In particular, the first operating element, in this case the front part 3, is rotated or screwed in, particularly preferably relative to the central part 5 and/or inner part 8. As a result of this operation, the top part 4 is moved with the opening or piercing element 4A axially to the carpule 2, so that the closure 2J of the carpule 2 is opened, in particular pierced. This opened or pierced state is shown in the schematic section according to FIG. 11 and the magnified detail shown in FIG. 12.

During the axial movement of the top part 4 or piercing element 4A towards the carpule 2, the carpule 2 or its housing 2E is preferably supported at the other end on the inner part 8 or the like, so that the frictional engagement between the ring section 4B and the outlet end of the carpule 2 is overcome, and the carpule 2 is pushed with its outlet end into the top part 4 or, conversely, the top part 4 is pushed onto the carpule 2.

It should be noted that both in the preassembled state, as shown in FIGS. 1 and 2, and in the open state, as shown in FIGS. 11 and 12, the first piston 2G of the carpule 2 is not yet actuated, i.e. has not yet been pushed in or moved along.

It should be noted that, starting from the preassembled state, a somewhat greater force has to be applied initially when rotating the first operating element or front part 3 in order to overcome the latching effected by engagement of the projection 5B in the latching recess 3C, as indicated previously.

It is also possible for further latching recesses 3C or the like to be provided or arranged along the thread turn of the external thread 3A, to form a kind of ratchet, so that it is impossible to rotate back in the opposite direction, which would be undesirable. However, other design solutions are also possible here.

Figure 13:
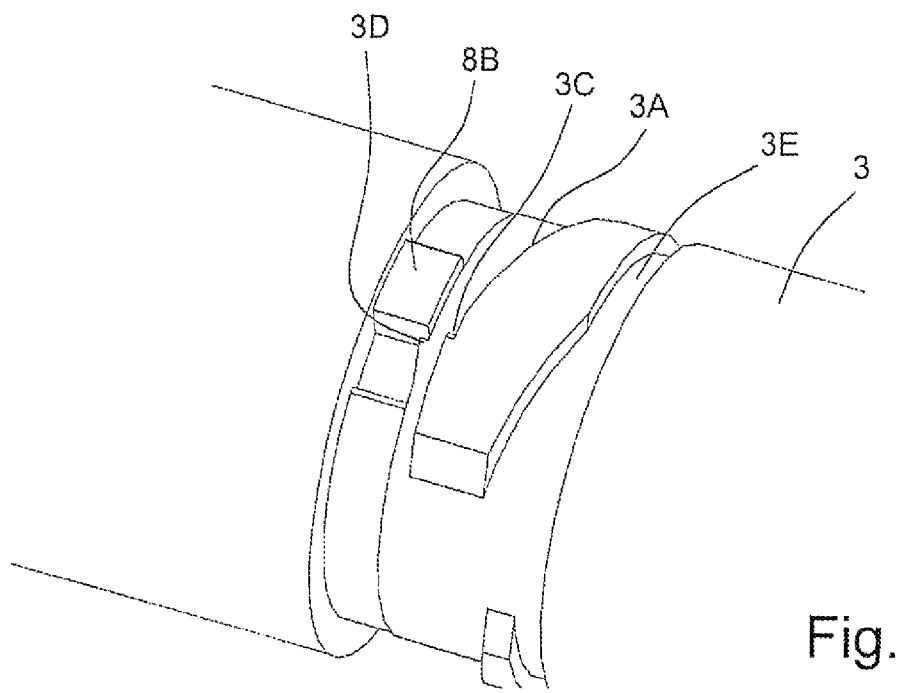
FIG. 13 is a detailed schematic view of the latching of the front part to the inner part.

When the movement in direction A, i.e. the opening operation, has ended, the first operating element or front part 3 preferably latches with the inner part 8, as shown schematically in FIG. 13 in particular, such that the front part 3 is, or has been, coupled for rotation with the inner part 8 in the opposite direction of rotation according to arrow B (cf. FIG. 1). In other words, when the first operating element or front part 3 of the apparatus 1 is rotated in the opposite direction or in direction B (operating movement B opposite to A), the inner part 8 is then rotated with it.

For the above-mentioned latching or rotary coupling the front part 3, in the embodiment shown, preferably has an axial undercut, abutment or projection 3D which, after moving past, comes to abut on a radial projection 8B of the inner part 8 (this passing movement being made possible by elastic material deformation) in order to achieve the desired rotary coupling in the opposite direction.

As the movement in direction A or the screwing in of the front part 3 ends, the front part 3 is preferably screwed fully onto the inner part 8 or into the device 1 or the central part 5.

The outer thread 3A of the front part 3 is preferably embodied such that, in the fully screwed in state, the front part 3 is freely rotatable in the central part 5, i.e. without the latter being axially unscrewed again. For this purpose the front part 3 or external thread 3A is provided in particular with a corresponding clearance 3E, as shown in FIG. 13.

The inner part 8 is preferably accommodated in the device 1 or in the housing part 5 such that it can be moved or rotated in only one direction; specifically, in the embodiment shown, only in the opposite direction to the direction of opening, or in direction B, as is apparent particularly from the representation according to FIG. 14. FIG. 14 is a schematic section along the line XIV-XIV in FIG. 2, in which the actuating part 9 has been omitted for reasons of clarity; the device 1 or the central part 5 in the embodiment shown preferably has a fixed abutment 5C, so that the inner part 8 can rotate or move only in one direction, in this case direction B, away from the abutment 5C in the device 1 or in the central part 5. In particular, the abutment 5C cooperates with the projection 8B of the inner part 8 so that opposite movement or rotation is blocked.

The inner part 8 is located in the rotary position shown in FIG. 14, starting from the preassembled state, up to the end of opening. In particular, the inner part 8 is held in this rotary position, and in the embodiment shown is preferably held as a result of a corresponding latching elevation 5D on the housing part 5, so that even if the front part 3 is rotated backwards in direction B before reaching the fully screwed-in state 5 or being fully opened, only the front part 3 is unscrewed again or unscrewed from the inner part 8, but the inner part 8 does not rotate with it in direction B. Rather, this co-rotation in direction B only takes place after corresponding latching or rotary connection of the front part 3 to the inner part 8, as already explained with reference to FIG. 13. Only as a result of this latching or rotary connection can a sufficiently high rotary force be exerted on the inner part 14, so that the projection 8B can overcome the latching elevation 5E, particularly by corresponding material deformation, and the inner part 8 is co-rotated with the first operating part or front part 3 in the opposite direction or in direction B.

After opening, the above-mentioned mixing is carried out by operating the first operating element or front part 3 in a different operating direction, particularly in the opposite direction, particularly preferably by rotating in direction B. This rotation is preferably irreversible. In the embodiment shown, this is achieved by having latching lugs 5E projecting radially inwardly on the central part 5 and forming undercuts or abutments or being embodied as serrations, so that these can be overcome by the projection 8B of the inner part 8 by elastic material deformation, but preventing or blocking reverse rotation in the direction B. However, other design solutions are also possible.

Thus, an operating action is used for mixing that is other than or different from that used for opening. In particular, the same operating element, namely the front part 3, is moved, in particular rotated, in one direction of movement A for opening and in the opposite direction of movement B for mixing.

The rotation of the inner part 8 in direction B causes the desired mixing to take place by the movement of the actuating part 9 into the carpule 2 and/or by the displacement of the first piston 2G. The manner in which this is preferably carried out in the embodiment shown will be explained hereinafter.

The actuating part 9 is preferably in the form of a ram and/or is axially adjustable or movable or displaceable. A front region or a region of the actuating part 9 adjacent to the carpule 2 passes through the inner part 8 or an opening 8C in the inner part 8, shown in FIG. 14, for example, and extends into the carpule 2, in order to displace the piston 2G as necessary or push the carpule 2. This region of the actuating part 9 is connected for rotation with the inner part 8, but engages in axially movable manner therewith. Preferably, this region therefore has a non-round outer contour and/or one that is provided with projections and indentations, which is guided in rotationally connected manner in complementary indentations, projections or the like in the opening 8C in the inner part 8. This opening 8C is penetrated by the above-mentioned region of the actuating part 9, as may be seen for example from FIGS. 1 and 11.

The actuating part 9 is provided, in another region, particularly in the region of its end remote from the carpule 2, with at least one radial projection, an external thread 9A or the like that engages with an internal thread 7A, formed, in particular, in or on the rear part 7, such that, as the actuating part 9 is rotated relative to the rear part 7, in this case in direction B (through the inner part 8), the actuating part 9 is moved axially towards the carpule 2 or into the carpule 2. The mating thread, in this case the internal thread 7A on the rear part 7, is preferably held in rotationally connected manner, in particular by holding or blocking the rear part 7 on the device 1 so as to rotate therewith. In other words, during the mixing or rotation in direction B, the actuating part 9 advances in a screwing movement, while the carpule 2, in particular, together with the actuating part 9, inner part 8 and/or front part 3 is rotated accordingly, so that preferably no relative rotations or torsional forces are produced.

Particularly preferably, a dual-action threaded engagement is provided between the actuating part 9 and the device 1 or the rear part 7.

During the operating movement in direction B or during the rotation in direction B or during mixing, the actuating part 9 is moved into the carpule 2 or the first piston 2G is pushed along, so that the liquid 2C is transferred from the first chamber into the second chamber 2D, while initially the second piston 2H in particular is moved somewhat downwards or towards the outlet, until the liquid 2C reaches the overflow channel 2F and is able to flow through this into the second chamber 2D or to the medicament 2E contained therein. This overflowing of the liquid 2C and mixing take place, particularly preferably, with the outlet 4C directed upwards to some extent, so that any air present in the carpule 2 can escape through the closure 2J that has been opened during opening; specifically, in the embodiment shown, through the piercing element 4A, the outlet 4C and/or the adjacent intake member 4E.

FIG. 15 shows the final state reached after mixing. The liquid 2C has been transferred into the second chamber 2D. The first piston 2G has been pushed along until it abuts on the second piston 2H, in particular. In this state the second piston 2H may optionally also have been pushed somewhat further into the carpule 2.

After the transferring or overflowing of the liquid 2C, it may mix with the medicament 2E, more particularly may dissolve the medicament 2E. This may optionally take place automatically or be assisted by shaking or the like.

After the liquid 2C has been transferred into the second chamber 2D, it may optionally be desirable to wait a while until the medicament 2E has dissolved. The mixing can preferably be monitored visually or is visible. In particular, the front part 3 and the carpule housing 2I may be at least partly or wholly transparent for this purpose.

FIG. 16 shows, in a magnified detail, that the actuating element 9 at the end of the operating movement B or the mixing has preferably not yet reached the axial end of the internal thread 7A.

The movement or rotation in direction B, i.e. the operating movement B, preferably takes place through less than 360°, for example through about 270° to 320°. In particular, the actuating part 9 is not fully axially advanced or screwed forwards in the internal thread towards the carpule 2. Rather, further axial movement of the actuating part 9 is still possible by rotation relative to the internal thread 7A during the next operating movement, namely during priming, which will be discussed in more detail hereinafter.

The rear part 7 preferably forms a (further or second) operating element of the device 1 and can be moved or operated particularly for priming and delivery, particularly in a first operating movement or direction C, particularly preferably by rotation, and/or in a second, different operating movement or direction, particularly preferably in the axial direction D.

During the opening and/or mixing or during the operating movements A and/or B, the second operating element or rear part 7 is preferably blocked or prevented from operation or movement and/or from rotation or twisting and/or axial movement. In the embodiment shown, this is preferably achieved by means of at least one radial projection 7B of the rear part 7, which is held in rotation-locked manner in a preferably axially open recess 6A in the insert 6, as shown in the schematic representation according to FIG. 17. In particular, the projection 7B is held by a retaining elevation 6B in the recess 6A in such a way that, when the end face of the inner part 8 abuts axially flat on the insert 6, the projection 7B cannot overcome the retaining elevation 6B in the direction of rotation C, but is secured for rotation by interlocking engagement. Moreover, the smooth end face of the inner part 7 then preferably forms an axial abutment for the projection 7B, so that the rear part 7 is secured or blocked in correspondingly axial manner against being pressed in or moved axially or moved in the direction D.

Figure 17:
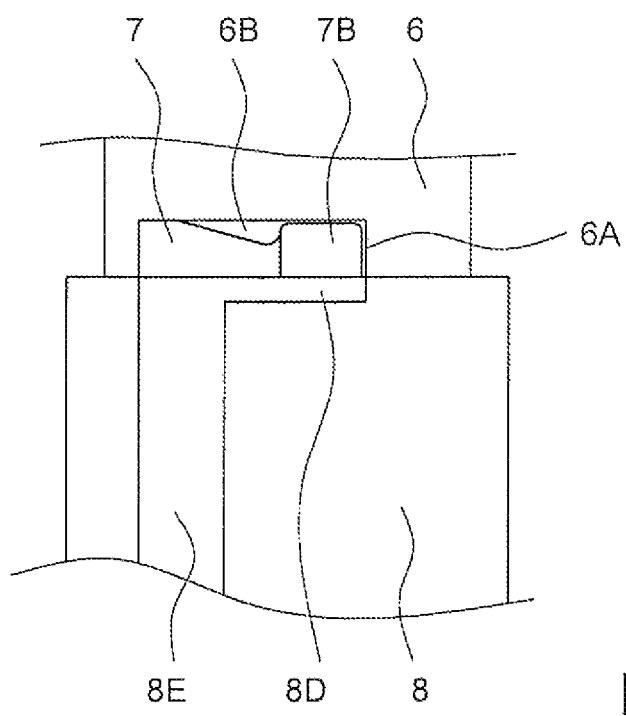
FIG. 17 is a schematic detailed view of a rotary blocking of the rear part by the insert and inner part.

Only when the rotary position shown in FIG. 17 of the inner part 8 relative to the insert 6 or to the recess 6A is achieved, after mixing, does an axial recess 8D of the inner part 8 come to rest adjacent to the recess 6A so that, for priming, an operating movement in direction C or rotation of the rear part 7 in direction C, particularly in the event of a slight axial inward pressure, is made possible, as in this way the projection 7B can be moved past the retaining elevation 6B, i.e. can be moved circumferentially in or along the recess 6A.

The above-mentioned operating movement C or the above-mentioned rotation of the rear part 7 in direction C leads to the desired priming, in that the internal thread 7A is (further) rotated or twisted relative to the actuating part 9 or its external thread 9A, as a result of which the actuating part 9 guided in rotationally connected manner by the inner part 8 is moved or pushed axially (further) forward and as a result the first piston 2G and accordingly the second piston 2H as well are moved or advanced or pushed axially further forward. Accordingly, any air located in the second chamber 2D or in the carpule 2 and/or in the outlet 4C can be displaced or expelled by the liquid medicament formulation 2A. The medicament formulation 2A is preferably taken up or aspirated directly by the intake member 4E. The priming thus preferably takes place with the cover 4D in place or not yet removed.

At the end of the operating movement in direction C, the inner part 8 preferably reaches its second end position in the direction of rotation B. In particular, in the embodiment shown, the projection 8B is held between the projection 5B and the next adjacent latching lug 5E, thus in particular on the right hand side of the projection 5B, according to FIG. 14.

FIG. 18 shows, in schematic section, the state after priming. The actuating part 9 and the pistons 2G and 2H have been advanced rather more in the axial direction or moved towards the outlet 4C. The cover 4D of the device 1 can now be removed or opened and the actual expulsion or delivery of the liquid medicament formulation 2A through the outlet 4C can take place. This is particularly preferably done by means of another (different) operating movement D. This extends in particular in a different direction than the operating movement C for priming. This is preferably carried out again with the same operating element, in this case by means of the rear part 7. Particularly preferably, there is an axial or linear movement, particularly a linear or axial pressing of the rear part 7 into the device 1 or the central part 5, as indicated by arrow D in FIG. 1, in particular.

In order to enable the above-mentioned axial movement or movement of the rear part 7 in direction D and hence of the actuating part 9 and the piston 2G and 2H in direction D, the rear part 7 or its projection 7B has to be freed in the axial direction D. In the embodiment shown this is preferably achieved by the fact that after the priming, by movement or rotation in direction C, the projection 7B comes to rest axially adjacent or on an extension of an axial groove 8E of the inner part 8 (the axial groove 8E is shown in FIG. 17), so as to enable axial movement in direction D.

In the embodiment shown, projections 7B are preferably formed on opposite sides. Accordingly, two recesses 6A, retaining elevations 6B, recesses 8D and/or axial grooves 8E are then also formed in each case.

However, other design solutions are theoretically also possible for achieving the desired blocking and release.

As a result of the operating movement D or the axial pressing in of the (second) operating element or rear part 7, the liquid medicament formulation 2A is expelled or delivered from the device 1 or carpule 2 in the desired manner, particularly preferably through the outlet 4C or a connection formed thereby. Alternatively or additionally, delivery may also take place through a cannula, for example for direct injection or the like.

Figure 19:
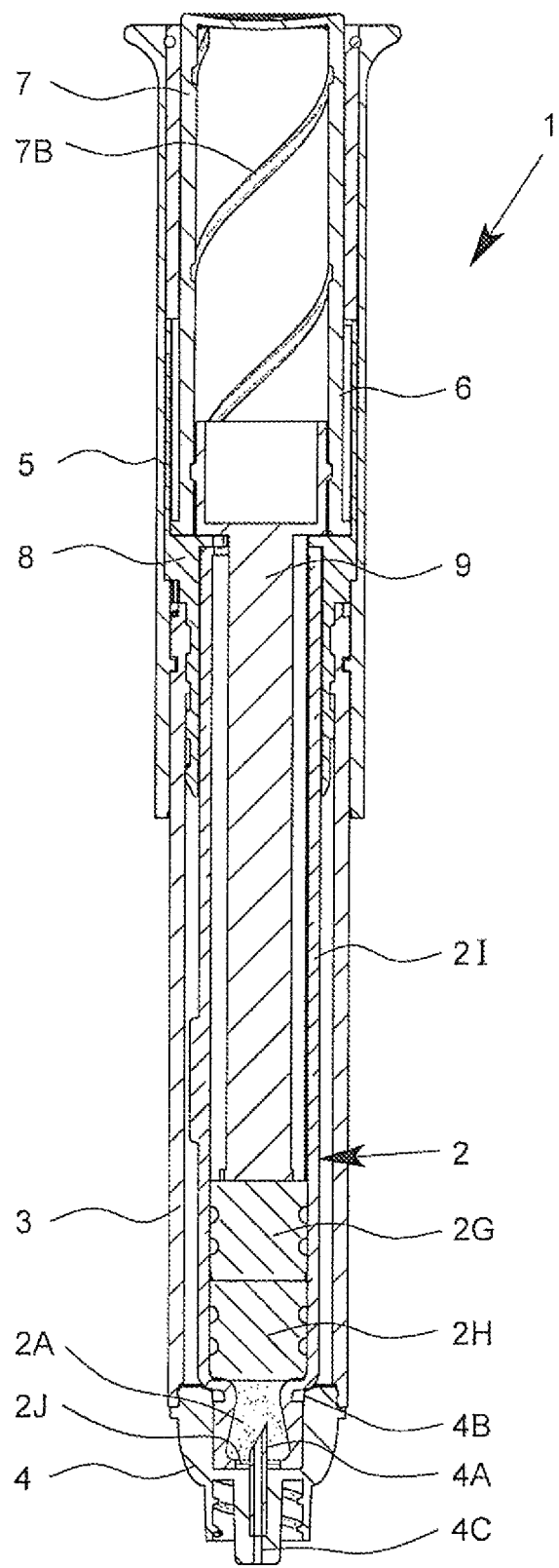
FIG. 19 is a schematic section through the device after the expulsion or discharging of the medicament formulation.

After the delivery or when the end position of the operating movement D has been reached, the second operating element or rear part 7 is preferably pressed substantially completely into the central part 5 or the housing of the device 1 or accommodated therein, in particular so that no further operation is possible, as can be seen from the schematic representation in FIG. 19, which illustrates the situation after the delivery. However, it is also acceptable if the rear part 7 and the actuating part 9 are pulled back again, as this does not move or pull the piston 2G back, i.e. there is no aspiration.

Particularly preferably, the actuating part 9 and the rear part 7 form a ram of the device 1, by means of which the carpule 2 is actuated or movement of the (first) piston 2G or the pistons 2G, 2H of the carpule 2 is made possible or carried out. In the embodiment shown, this ram is preferably of multi-part construction, in this case namely through the parts 7 and 9, and can be extended by rotation (particularly by rotation of the two parts 7 and 9 relative to one another). This enables satisfactory or simple handling. In particular, with a device 2 of compact design, this ensures that the user (not shown) does not have to change their grip and/or still has an adequate actuating surface.

Particularly preferably, the proposed device 1 can be operated so that the first unit or the first operating element, such as the housing part 3, can be grasped with one hand and the second unit or upper part or central part 5 can be grasped with the other hand, thus enabling the (second) operating element or rear part 7 to be operated with the thumb or another finger on the other hand without having to change one's grip. This therefore allows very simple and reliable operation.

The proposed device 1 and the proposed method are also particularly characterised in that operating movements in different directions or in opposite directions can be carried out one after the other and/or different operating elements such as the front part 3 on the one hand and the rear part 7 on the other hand can be operated one after the other, in particular in order to carry out various or different operations or steps, such as opening, mixing, priming and/or expulsion.

In another particular aspect of the present invention, using the proposed device 1 or using the proposed method, some or all of the operating movements and/or some or all of the processes or steps such as opening, mixing, priming and/or expulsion can be carried out or effected one after another and/or in defined manner.

Particularly preferably, for each operation or step such as opening, mixing, priming and/or expulsion, i.e. for different actuations of the carpule 2, another or a different operating movement or another direction of operation and/or another operating element is required. This promotes simple, intuitive and/or reliable operation or handling of the device 1.

The proposed device 1 is relatively simple, being made in particular of plastics parts or injection moulded parts and/or consisting of few parts.

Particularly preferably, the device 1 is provided with corresponding markings or symbols such as the arrows or pictograms shown in FIG. 1, for illustrating the operating movements or the actions required. The various markings are, in particular, numbered or labelled in some other way to show or illustrate to the user (not shown) the sequence that is desired or necessary.

It is also possible that individual markings are no longer visible after operation has taken place or after the corresponding operating action has been carried out. For example, after the front part 3 has been screwed into the central part 5, the first marking with the arrow A may disappear or be hidden by said central part 5. A user will then automatically or intuitively continue with the next operation or operating movement, in this case in direction B.

The proposed device 1 and the proposed method may also be used for other purposes, theoretically and according to a preferred variant, particularly for mixing substances and/or liquids in general and for delivery, for example for multi- or two-component systems or mixtures or blends, such as two-component adhesives. The carpule 2 will then accordingly contain other substances and/or liquids. If desired, priming may then be omitted as well.

| List of reference numerals: | |
|---|---|
| 1 | device |
| 2 | carpule |
| 2A | medicament formulation |
| 2C | liquid |
| 2D | second chamber |
| 2E | medicament |
| 2F | overflow channel |
| 2G | first piston |
| 2H | second piston |
| 2I | housing |
| 2J | closure |
| 3 | front part |
| 3A | external thread |
| 3B | internal thread |
| 3C | latching recess |
| 3D | projection |
| 3E | clearance |
| 4 | top part |
| 4A | piercing element |
| 4B | ring section |
| 4C | outlet |
| 4D | cover |
| 4E | intake member |
| 5 | central part |
| 5A | internal thread |
| 5B | projection |
| 5C | abutment |
| 5D | latching elevation |
| 5E | latching lug |
| 5F | recess |
| 6 | insert |
| 6A | recess |
| 6B | retaining elevation |
| 6C | projection |
| 7 | rear part |
| 7A | internal thread |
| 7B | projection |
| 8 | inner part |
| 8A | external thread |
| 8B | projection |
| 8C | perforation |
| 8D | recess |
| 8E | axial groove |
| 9 | actuating part |
| 9A | external thread |
| A | movement or direction of operation |
| B | movement or direction of operation |
| C | movement or direction of operation |
| D | movement or direction of operation |

The invention claimed is:

1. A device (1), comprising:
a carpule (2) having: (i) a substantially tubular housing (2I) defining an inner volume, a longitudinal axis of the device (1), an open proximal end, and a closed distal end; (ii) a piston (2G) slidably disposed within the inner volume of the housing (2I), and movable toward the distal end in order to expel a liquid from the carpule (2);
a front part (3) having a substantially tubular configuration defining an inner volume, a proximal end, and a distal end;
a central part (5) having a substantially tubular configuration defining an inner volume, a proximal end, and a distal end, where the proximal end of the front part (3) engages the distal end of the central part (5) such that the respective inner volumes of the front part (3) and the central part (5) communicate with one another and the carpule (2) is disposed therein;
an elongate actuating part (9), including a proximal end and a distal end that is engageable with the piston (2G) such that axial movement of the actuating part (9) along the longitudinal axis toward the distal end of the housing displaces the piston (2G) and the liquid toward the distal end of the housing; and
a mechanism configured to influence the engagement of the proximal end of the front part (3) and the distal end of the central part (5), such that:
(a) rotation of the front part (3) relative to the central part (5) in a first direction (A) causes the front part (3) to telescope into the central part (5) by a first predetermined axial movement along the longitudinal axis, and once the first predetermined axial movement is reached further rotation in the first direction (A) does not cause any further telescoping of the front part (3) into the central part (5); and
(b) after (a), rotation of the front part (3) relative to the central part (5) in a second direction (B), opposite to the first direction (A), causes the actuating part (9) to move by a second predetermined axial movement through the open proximal end of the carpule (2) and advance the piston (2G) and the liquid toward the distal end of the housing.

2. The device according to claim 1, wherein:
the mechanism includes a rear part (7) having a substantially tubular configuration defining an inner surface, a proximal end, and a distal end, where the proximal end of the central part (5) engages the distal end of the rear part (7);
the proximal end of the actuating part (9) threadingly engages the inner surface of the rear part (7); and
(c) after (b), rotation of the rear part (7) relative to the central part (5) in a third direction (C) places the device in a priming state, which causes the actuating part (9) to further move by a third predetermined axial movement through the open proximal end of the carpule (2) and further advance the piston (2G) and the liquid, such that at least some of the liquid forces any air out of the distal end of the housing.

3. The device according to claim 2, wherein after (c), axial movement of the rear part (7) telescopically into the central part (5) places the device in an expulsion state, which causes the actuating part (9) to further move by a fourth predetermined axial movement through the open proximal end of the carpule (2) and further advance the piston (2G) and the liquid, such that the liquid is expelled out of the distal end of the housing.

4. The device according to claim 3, wherein the device (1) is configured such that the opening, mixing, priming and expulsion states are effected by the successively different operating movements (a), (b), (c), and (d).

5. The device according to claim 1, wherein
the rotation of the front part (3) relative to the central part (5) in the first direction (A) to achieve the first predetermined axial movement of the front part (3) telescoping into the central part (5) places the device in an open state whereby the closed distal end of the housing (2I) opens; and the rotation of the front part (3) relative to the central part (5) in the second direction (B) to achieve the second predetermined axial movement of the piston (2G) and the liquid toward the distal end of the housing (2I) places the device in a mixing state in which the liquid mixes within the housing (2I) with either a dry medicament (2E) or a further liquid to produce a medicament (2A).

6. The device according to claim 5, wherein the device includes a cap (4) releaseably connectable to the housing (2I) and having a piercing element (4A) directed toward the distal end of the housing (2I), such that the rotation of the front part (3) relative to the central part (5) in the first direction (A) to achieve the first predetermined axial movement of the front part (3) telescoping into the central part (5) to place the device in the open state causes the piercing element to pierce the closed distal end of the housing (2I) and create an aperture therethrough for the liquid to exit.

7. The device according to claim 1, wherein:
the carpule (2) includes a further piston (2H) disposed within the inner volume defining a chamber between the piston (2G) and the further piston (2H) in which the liquid is disposed; and the carpule (2) includes a bypass channel, whereby the rotation of the front part (3) relative to the central part (5) in the second direction (B) to achieve the second predetermined axial movement of the piston (2G) to place the device in a mixing state, causes the actuating part (9) to move the piston (2G), the liquid, and the further piston (2H) such that the further piston (2H) and the liquid are proximate to the bypass channel, which permits the liquid to advance ahead of the further piston.

8. The device according to claim 7, wherein the carpule (2) is embodied as a multi-chamber carpule.

9. The device according to claim 1, wherein the mechanism operates in such a way that rotation of the front part (3) relative to the central part (5) in the second direction (B) is not permitted until after the rotation thereof in the first direction (A) causes the front part (3) to telescope into the central part (5) by the first predetermined axial movement along the longitudinal axis.

* * * * *